(12) United States Patent
Rea et al.

(10) Patent No.: US 7,560,105 B1
(45) Date of Patent: Jul. 14, 2009

(54) DENDRITIC CELLS ACTIVATED IN THE PRESENCE OF GLUCOCORTICOID HORMONES ARE CAPABLE OF SUPPRESSING ANTIGEN-SPECIFIC T CELL RESPONSES

(75) Inventors: Delphine Gabrielle Josette Rea, Leiden (NL); Cornelis Johannes Maria Melief, Haarlem (NL); Rienk Offringa, Leiden (NL)

(73) Assignee: Leids Universitair Medisch Centrum, Leiden (NL)

( * ) Notice: Subject to any disclaimer, the term of this patent is extended or adjusted under 35 U.S.C. 154(b) by 498 days.

(21) Appl. No.: 09/666,430

(22) Filed: Sep. 21, 2000

Related U.S. Application Data

(60) Provisional application No. 60/157,442, filed on Oct. 4, 1999.

(51) Int. Cl.
*A01N 63/00* (2006.01)
*A61K 39/00* (2006.01)
*A61K 38/00* (2006.01)
*C12N 5/00* (2006.01)
*C07K 2/00* (2006.01)

(52) U.S. Cl. .................. 424/93.71; 424/184.1; 435/325; 435/372; 435/375; 435/377; 435/373; 435/384; 514/2; 530/300

(58) Field of Classification Search .............. 424/93.71, 424/184.1, 26; 435/325, 372, 375, 377, 373, 435/384; 514/2; 530/300
See application file for complete search history.

(56) References Cited

OTHER PUBLICATIONS

Tisch, R and McDevitt, HO. Proc. Nat. Acad. Sci. (USA). 91-437-438. Jan. 1994.*
Steptoe, RJ and Thomson, AW. Clin. Exp. Immunol. 105:397-402. 1996.*
Slectman's Medical Dictionary "Glucocorticoid", "Steroid", "Metabolism", 2002.*
Marketletter, 1999, Marketletter Publications, London.*
Zhang, J.Z. et al. J. Neurol. 2002; 249:212-218.*
Auchincloss et al. in Fundamental Immunology, Paul ed., 1999, pp. 1182-1185.*
Bray, M.T., et al. Br. J. Pharmacol. Aug. 1978;63(4):635-642.*
Cronstein et al., A mechanism for the antiinflammatory effects of corticosteroids: The glucocorticoid receptor regulates leukocyte adhesion to endothelial cells and expression of endothelial-leukocyte adhesion molecule 1 and intercellular adhesion molecule 1, Proc. Natl. Acad. Sci., Nov. 1992, pp. 9991-9995, vol. 89, USA.
Greten et al., Direct visualization of antigen-specific T cells: HTLV-1 Tax11-19-specific CD8+ T cells are activated in peripheral blood and accumulate in cerebrospinal fluid from HAM/TSP patients, Proc. Natl. Acad. Sci., Jun. 1998, pp. 7568-7573, vol. 95, USA.
Hancock et al., Costimulatory function and expression of CD40 ligand, CD80, and CD86 in vascularized murine cardiac allograft rejection, Proc. Natl. Acad. Sci., Nov. 1996, pp. 13967-13972, vol. 93, USA.
Kampgen et al., Class II major histocompatibility complex molecules of murine dendritic cells: Synthesis, sialylation of invariant chain, and antigen processing capacity are down-regulated upon culture, Proc. Natl. Acad. Sci., Apr. 1991, pp. 3014-3018, vol. 88, USA.
Nicholson et al., Heteroclitic proliferative responses and changes in cytokine profile induced by altered peptides: Implications for autoimmunity, Proc. Natl. Acad. Sci. Jan. 1998, pp. 264-269, vol. 95, USA.
Steeme et al., T lymphocytes from human atherosclerotic plaques recognize oxidized low denisty lipoprotein, Proc. Natl. Acad. Sci, Apr. 1995, pp. 3893-3897, vol. 92, USA.
Abul K. Abbas, M.B.B.S. et. al., Cellular and Molecular Immunology, Antigen Presentation and T Cell Antigen Recognition, pp. 115-137, W. B. Sauders Co., Philadelphia, Pennsylvania, 1991.
AHFS Drug Information 91 pp. 1810, American Society of Hospital Pharmacists, Inc., Bethesda, Maryland, 1991.
Arthur J. Vander, M.D. et. al., Human Physiology: The Mechanisms of Body Function, Defense Mechanisms of the Body: Immunology, Foreign Chemicals and Stress, pp. 599-640, Mary Jane Martin and Susan Hazlett eds., McGraw-Hill Book Co. 4th ed. New York, New York, 1985.
Bruce Alberts et al., Molecular Biology of The Cell, The Immune System, 2nd ed. Garland Publishing, Inc., New York, New York, 1989, pp. 1044-1048.
King et al., Dictionary of Genetics, Fifth Edition, pp. 14, 332, Oxford University Press, New York, New York, 1997.
Goodman et al., Goodman and Gilman's The Pharmacological Basis of Therapeutics, (Seventh Ed.) Ch 63 Adrenocorticotrophic Hormone: Adrenocortical Steroids and their Synthetic Analogs: Inhibitors of Adrenocortical Steroid Biosynthesis, pp. 1459-1489, MacMillan Publishing Company, New York, New York, 1985.
Remington's Pharmaceutical Sciences, Lypressin, pp. 958-972, Mack Publishing Company, Easton, Pennsylvania, Alfonso R. Gennaro ed., 1985.

* cited by examiner

*Primary Examiner*—Eileen B O'Hara
*Assistant Examiner*—F. Pierre VanderVegt
(74) *Attorney, Agent, or Firm*—TraskBritt

(57) ABSTRACT

The present invention provides novel methods for immunotherapy. The invention provides immune cells and methods to generate them, with the capacity to at least in part reduce an immune response in a host. In one aspect, the invention provides a method for generating a dendritic cell with the capacity to tolerize a T-cell for antigen the T-cell was specific for including culturing peripheral blood monocytes from an individual to differentiate into dendritic cells, activating the dendritic cells in the presence of a glucocorticoid hormone and loading the activated dendritic cell with the antigen the T-cell was specific for.

43 Claims, 6 Drawing Sheets

DENDRITIC CELLS ACTIVATED IN THE PRESENCE OF GLUCOCORTICOID HORMONES ARE CAPABLE OF SUPPRESSING ANTIGEN-SPECIFIC T CELL RESPONSES

REFERENCE TO RELATED APPLICATION

This application claims priority from Provisional Application Ser. No. 60/157,442, filed Oct. 4, 1999.

TECHNICAL FIELD

The invention relates to the field of medicine. More in particular, the invention relates to the field of immunotherapy.

BACKGROUND OF THE INVENTION

The remarkable immunostimulatory properties of dendritic cells ("DC") reside in their ability to transport antigens from peripheral tissues to lymphoid organs where they present these antigens to T-cells in an optimal costimulatory context (1). To achieve this complex sequence of events, DC exist in different functional stages. Immature DC behave as sentinels in peripheral tissues where they efficiently capture antigens. Upon pathogen invasion, induction of protective T-cell responses require the activation of immature DC into mature immunostimulatory cells. DC activation is triggered in inflamed tissues by cytokines such as IL-1 and TNF-a and by bacterial components such as lipopolysaccharide (LPS) (2, 3). Activated DC migrate to T-cell areas in the lymph nodes while upregulating their costimulatory capacities and optimizing their antigen presenting functions. Upon interaction with antigen-specific T-cells, DC activation is further completed through engagement of the receptor-ligand (1) pair CD40-CD40L, leading to the production of IL-12 (4, 5, 6), a key cytokine for T helper (Th) type 1 and cytotoxic T lymphocyte (CTL) priming (7).

Antigen Presenting Cell (APC) activation through CD40-CD40L interactions represents an important immunoregulatory step for the establishment of protective T-cell immunity against pathogens and tumors (8, 9, 10). This process also plays a key role in the onset of destructive T-cell-mediated disorders such as autoimmune diseases, allograft rejection and graft versus host disease (11, 12, 13). The current treatment of these disorders largely relies on the administration of glucocorticoids (the abbreviation "GC" is used herein for the terms "glucocorticoids" and "glucocorticoid"), which exert potent anti-inflammatory and immunosuppressive effects. Because GC negatively interfere with many aspects of T-cell activation, such as IL-2-driven proliferation and inflammatory cytokine production (reviewed in 14), activated T-cells have long been considered as the main targets for GC action. Several lines of evidence now suggest a role for DC in GC-induced immune suppression. Moser et al. (15) found that GC prevented the spontaneous activation of murine DC thereby decreasing their T-cell stimulatory potential. Kitajima et al. (16) showed that GC could hamper the T-cell-mediated activation of a murine DC line. Viera et al. reported that human DC exposed to GC were poor producers of IL-12 upon LPS stimulation (17). These findings only concern loss of typical DC features and, therefore, favor a simple inhibitory role of GC on DC activation. A more complex immunoregulatory action on the DC system has not been considered.

The present invention resulted from a detailed analysis of the impact of GC on the CD40-mediated activation of monocyte-derived DC. These DC develop after culture with GM-CSF and IL-4 (2, 18) or after transmigration through endothelial cells (19) and are known to mature into the most potent human Th1-type-inducing APC upon CD40 ligation (5, 20). Moreover, these APC can easily be generated in large numbers and are thereby the cells of choice for DC-based modulation of T-cell immunity (21, 22). In contrast to previous studies, the present invention shows that GC, such as dexamethasone (DEX), do not merely prohibit DC activation but converts CD40 ligation on human monocyte-derived DC and is transformed into an alternative activation pathway. DEX profoundly affects the CD40-dependent maturation of human monocyte-derived DC, not only by preventing the upregulation of costimulatory adhesion and MHC surface molecules, but also by causing these cells to secrete the anti-inflammatory mediator IL-10 instead of the Th1 stimulatory cytokine IL-12. In agreement with these phenotypic and functional changes, DC triggered through CD40 in the presence of DEX are poor stimulators of Th1-type responses. Most importantly, the present invention shows that such DC are able to induce a state of hyporesponsiveness in Th1 cells, indicating that these cells are capable of active suppression of Th1-type immunity.

SUMMARY OF THE INVENTION

As mentioned above, the impact of GC on DC has been the subject of several previous studies by others. However, in contrast with the present invention, these studies only highlighted inhibitory effects of GC on the DC system DEX was found to block the upregulation of CD80, CD86 and MHC class II molecules upon activation of murine spleen DC (15, 16), whereas very recently DEX was demonstrated to also prevent the differentiation of DC from monocyte precursors (28). In these studies, the inability of DC to acquire high expression of costimulatory and MHC molecules was accompanied with a decrease in their T-cell stimulatory potential, but the effect of GC on IL-12 production was not investigated. On the other hand, Viera et al. found that the effect of GC on LPS-induced DC activation consisted in a 4-fold reduction of IL-12p70 synthesis (17). This partial effect on IL-12 secretion contrasts with the complete suppression of IL-12p70 production which is the subject of the present invention and can be explained by the fact that their GC-treated immature DC were extensively washed prior to LPS stimulation. We indeed found that upon removal of GC, the effects of these drugs on immature DC were rapidly reversible. The continuous presence of GC during CD40 triggering of DC was clearly preferred in order to stably and completely modulate DC activation (data not shown). Taken together, previous findings indicated that the impact of GC on the DC system should be merely interpreted as an inhibitory event. Importantly, the present invention clearly demonstrates that GC, such as DEX do not simply suppress DC activation but rather redirect this process towards a distinct functional program.

DC activation through engagement of CD40-CD40L is a key stimulatory event for the generation of effective Th1 and CD4-dependent CTL responses in vivo (10, 36, 37, 38). This pathway, however, is also involved in the development of unwanted T-cell responses leading to autoimmune disease or organ-transplant rejection (11, 12, 13). Until now, treatment of patients suffering from such disorders largely relied on the systemic administration of GC hormones. This treatment does not only suppress pathogenic T-cell responses, but also induces a general state of immunosuppression and metabolic and endocrine side effects. The present invention demonstrates that activation of human monocyte-derived DC through CD40, in the presence of GC such as DEX, results in an IL-10-producing APC that is a poor stimulator for Th1-type responses and that can even confer hyporesponsiveness to Th1 cells. The present invention, therefore, indicates that such DC loaded with appropriate antigens can be exploited as a novel approach for specifically downregulating unwanted T-cell responses in vivo.

Seven days immature DC were cultured for 24 h in the absence or the presence of $10^{-6}$ M DEX and activated via CD40 with the CD8-CD40L fusion protein for 48 h. The comparison with immature DC maintained in medium alone is shown. Empty histograms show the background staining with isotype controls MoAb and solid histograms represent specific staining of the indicated cell surface markers. Specific mean fluorescence intensities are indicated. Mean fluorescence intensities of isotype controls were between 3 and 4. Data are representative of 4 independent experiments.

Figure 2:
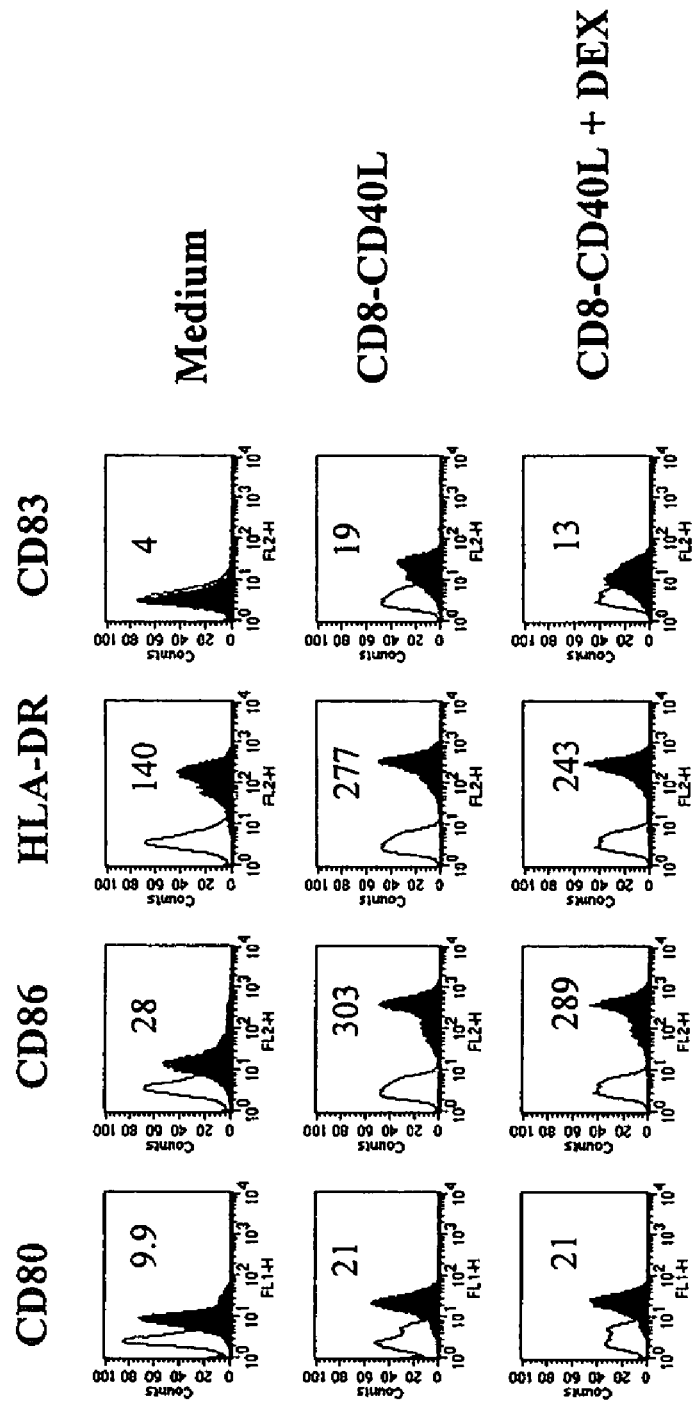

FIG. 2. DC triggered through CD40 maintain an activated phenotype upon a subsequent DEX exposure. Immature DC were activated with the CD8-CD40L fusion protein. DEX ($10^{-6}$ M) or medium control were added 48 h later and cells were analyzed after 2 additional days of culture. The comparison with immature DC maintained in medium alone is shown. Empty histograms show the background staining with isotype controls MoAb and solid histograms represent specific staining of the indicted cell surface markers. Specific mean fluorescence intensities are indicated. Mean fluorescence intensities of isotype controls were between 3 and 5. Data are representative of 2 independent experiments.

Figure 3:
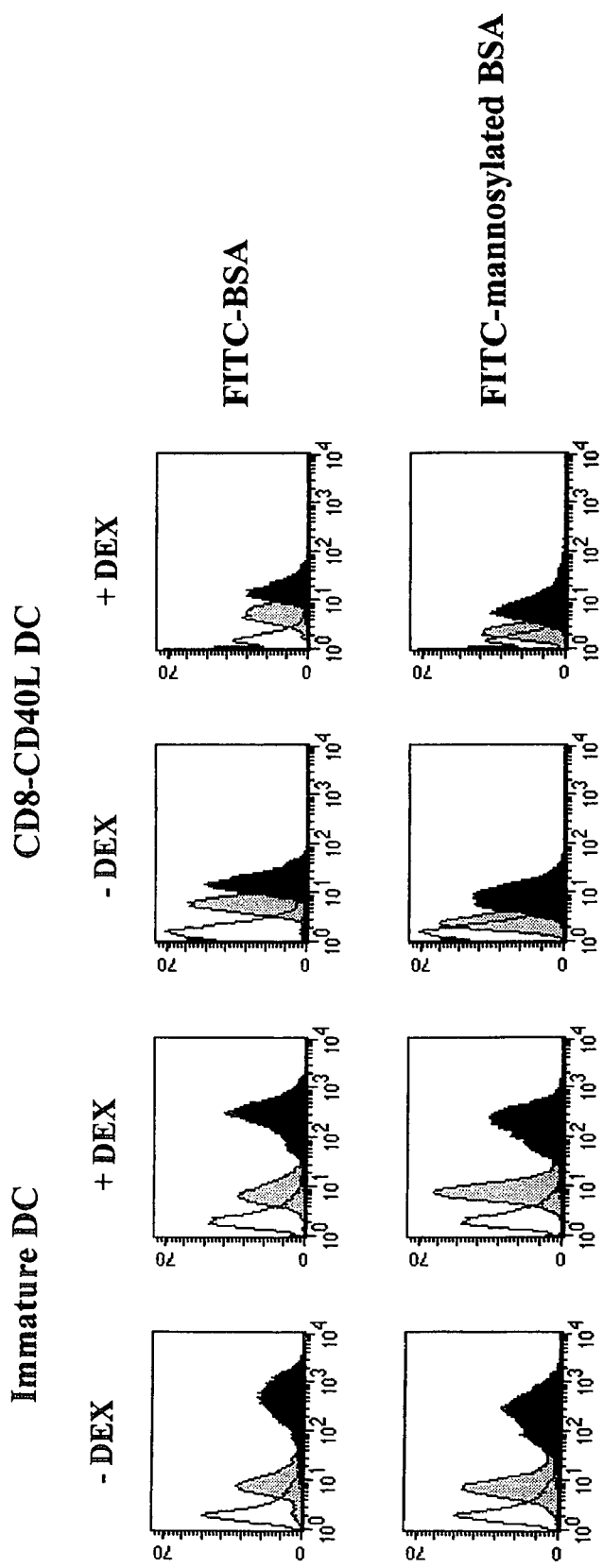

FIG. 3. Pretreatment with DEX does not affect the regulation of DC antigen uptake machinery. Immature DC were incubated in the absence or the presence of $10^{-6}$ M DEX for 24 h and further activated or not via CD40 with the CD8-CD40L fusion protein for 48 h. Cells were pulsed for 1 h with medium containing either 1 mg/ml FITC-BSA or 1 mg/ml FITC-mannosylated BSA. Empty histograms show the background autofluorescence, Grey-filled histograms show the background uptake at 0° C. and black-filled histograms show the specific uptake at 37° C. Data are representative of 3 independent experiments.

Figure 4:
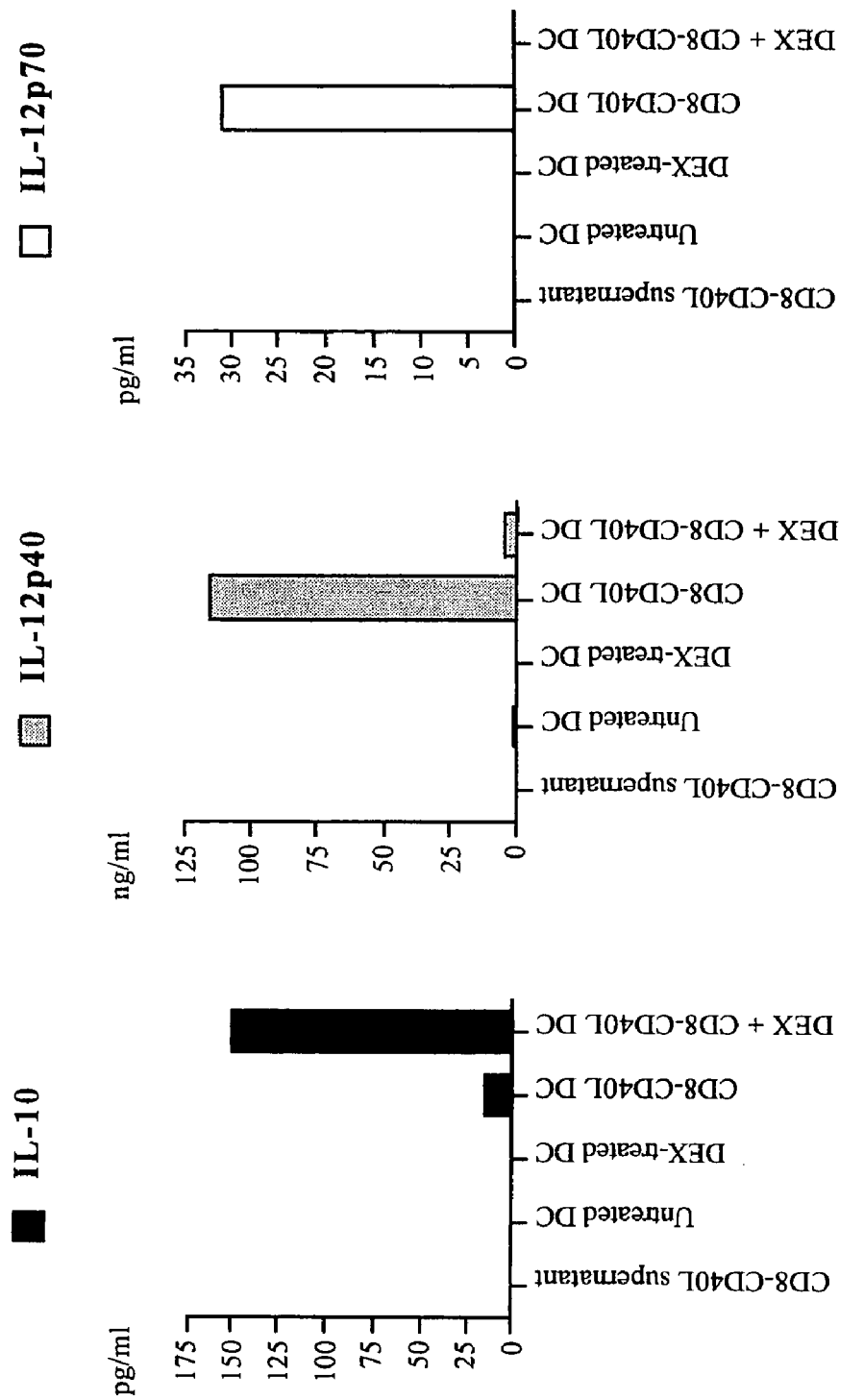

FIG. 4. Pretreatment with DEX alters the cytokine secretion profile of CD40-triggered DC.

DEX-exposed or control immature DC were left in culture without further treatment or stimulated with the CD8-CD40L fusion protein Culture supernatants were harvested 48 h later and IL-10, IL-12p40 and IL-12p70 secretion were analyzed by specific ELISA. Data are representative from 6 independent experiments.

Figure 5:
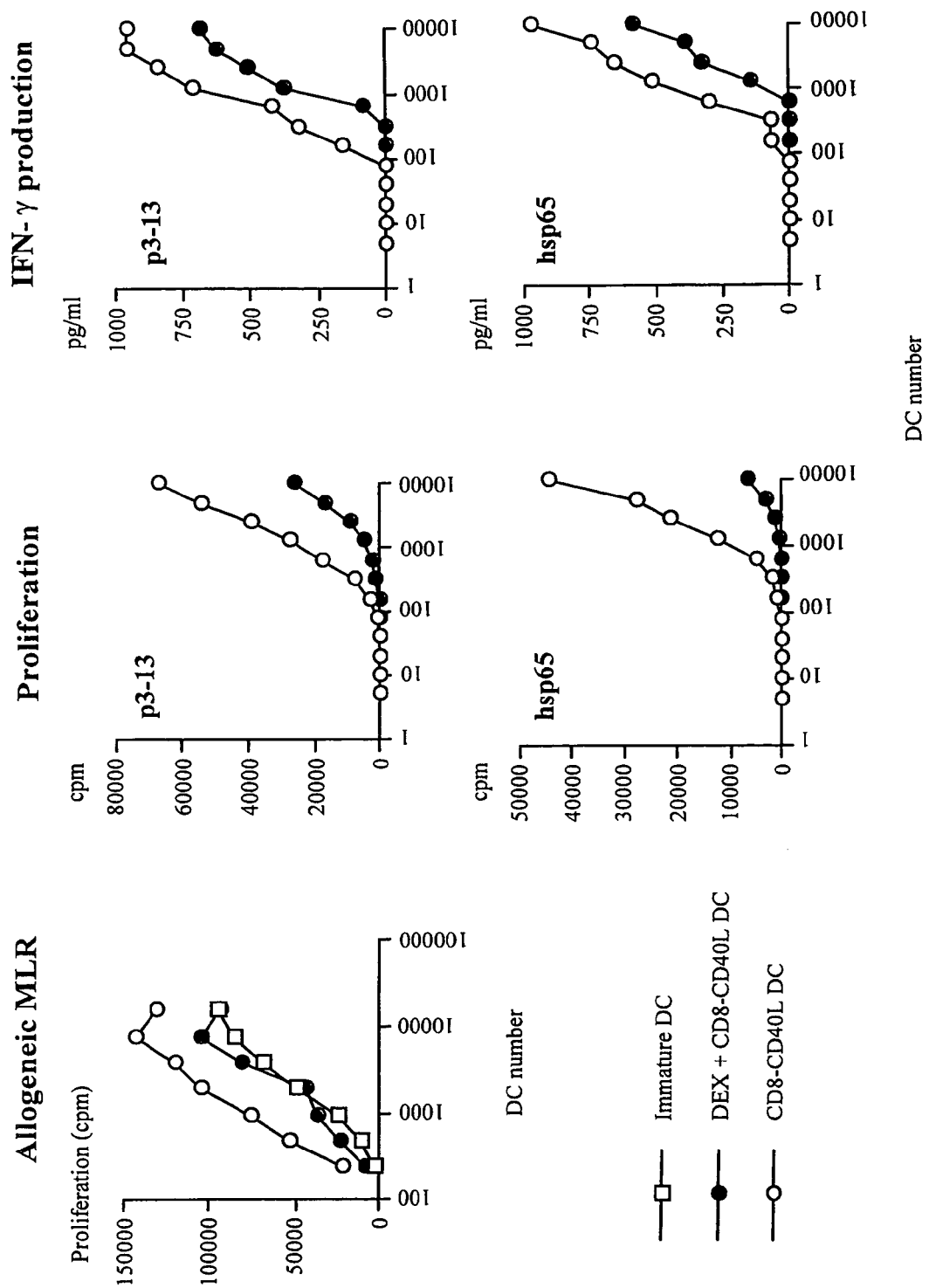

FIG. 5. Pretreatment with DEX impairs the T-cell stimulatory capacities of DC activated via CD40 and leads to a state of hyporesponsiveness of Th1 cells.

Allogeneic MLR: nonadherent allogeneic PBMC were cultured with different numbers of CD40-triggered DC, DEX-treated CD40-triggered DC or immature DC. The proliferative response was measured on day 5.

Th1 stimulation assays: Hsp65-specific T-cells were cultured with different numbers of HLA-DR matched CD40-triggered DC or with DEX-treated CD40-triggered DC pulsed with the hsp65 protein or with the specific p3-13 peptide epitope. The proliferative response and the T-cell dependent IFN-g production were analyzed on day 3. Data are representative of 4 independent experiments.

Figure 6:
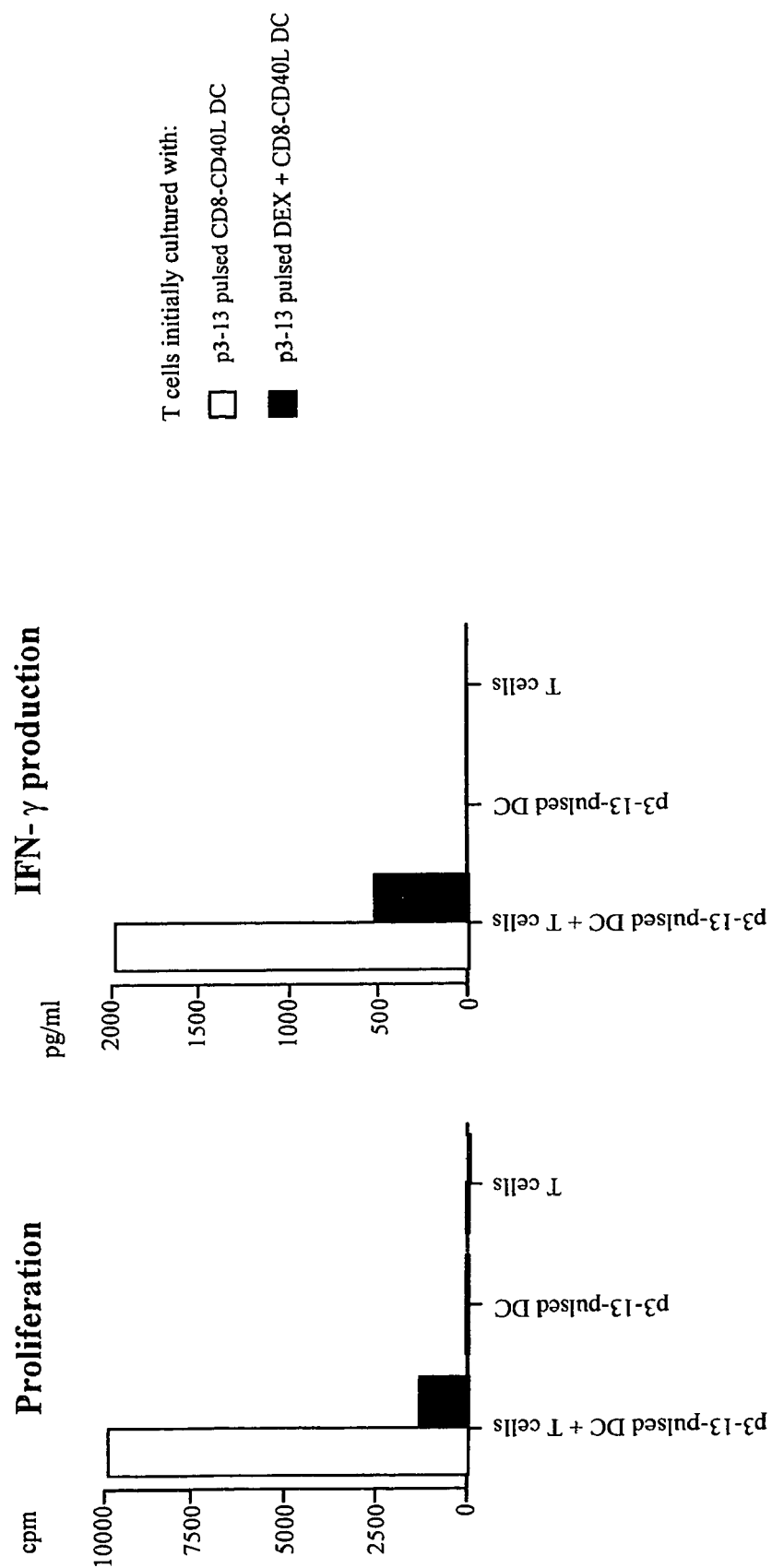

FIG. 6. DEX-treated DC triggered through CD40 induce a state of hyporesponsiveness in Th1 cells. Hsp65-specific T-cells precultured with CD40-triggered DC or with DEX-treated CD40-triggered DC pulsed with the p3-13 peptide epitope were harvested after 48 h, allowed to rest in the presence of 5 U/ml IL2 for 3 days, and restimulated with p3-13-pulsed DC. The proliferative response and IFN-g production were measured on day 3. Similar results were obtained in 2 independent experiments.

DETAILED DESCRIPTION OF THE PREFERRED EMBODIMENTS

The dendritic cells of the invention possess different capabilities than those previously reported for dendritic cells. One can, therefore, consider these cells to be part of a class of cells distinct from the class formed by the "classical" dendritic cells. The dendritic cells of the invention can be used in a different way than the classical dendritic cells. The dendritic cells of the invention can, for instance, be used to suppress, at least in part, an undesired immune response in a host. In one aspect, the invention, therefore, provides a method for preparing a pharmaceutical composition for reducing an unwanted T-cell response in a host, comprising culturing peripheral blood monocytes from the host to differentiate into dendritic cells, activating said dendritic cells in the presence of a glucocorticoid hormone and loading the activated dendritic cells with an antigen against which the T-cell response is to be reduced. An unwanted T-cell response can be any type of T-cell response. For instance, but not limited to, a T-cell response associated with an autoimmune disease or a transplantation disease, such as a graft versus host disease or a host versus graft disease. A pharmaceutical composition of the invention typically comprises a dendritic cell of the invention suspended in a liquid suitable for preserving the function of the dendritic cell in the liquid and/or suitable for administration to a host. A host, preferably, is a human. Preferably, the host is at risk of developing or is suffering from an autoimmune disease or allergy. Preferably, the host suffers from or is at risk of suffering from a host versus graft disease and/or a graft versus host disease. With the term "at risk," it is meant that one expects that the host may develop the disease, for instance, but not limited to, a host receiving a transplant. Such a host is considered to be at risk of developing a host versus graft disease. An antigen typically is a peptide capable of binding to a major histocompatibility complex (MHC) I and/or II molecule. Such peptides are known in the art and a person skilled in the art is capable of determining whether a given peptide comprises an antigen or not. An antigen may be derived from a naturally occurring protein. An antigen may also be a synthetic peptide or equivalent thereof preferably with an amino-acid sequence equivalent to a peptide derived from a protein.

In another aspect, the invention provides a pharmaceutical composition for reducing an unwanted T-cell response in a host, the composition being obtained by culturing peripheral blood monocytes from the host to differentiate into dendritic cells, activating the dendritic cells in the presence of a glucocorticoid hormone and loading the activated dendritic cells with an antigen against which the T-cell response is to be reduced. In one embodiment, a method is provided for reducing an unwanted T-cell response in a host comprising administering a composition of the invention to the host.

The invention further provides a method for reducing an unwanted T-cell response in a host comprising culturing peripheral blood monocytes from the host to differentiate into dendritic cells, activating the dendritic cells and/or their precursors in the presence of a glucocorticoid hormone and loading the activated dendritic cells with an antigen against which the T-cell response is to be reduced and administering the composition to the host.

In one embodiment of the invention, the activation is done through a CD40 receptor. Activation of DC through triggering of the CD40 receptor can involve either incubation with a CD8-CD40L fusion protein, a trimeric form of CD40L consisting of CD40L-molecules to which a modified leucine zipper has been attached, anti-CD40 antibodies, or cells that express CD40L. Other signals that can be employed for the activation of DC as described in the present invention include lipopolysaccharide (LPS) and polyI/C.

In another aspect, the invention provides a method for obtaining a dendritic cell capable of tolerizing a T-cell for an antigen comprising providing the dendritic cell with a glucocorticoid hormone, activating the dendritic cell and providing the dendritic cell with the antigen. With the term "tolerizing," it meant that the dendritic cell has an immunosuppressive effect on the T-cell. A tolerized T-cell essentially will not respond with cell division when exposed to a cell presenting an antigen, a T-cell in the untolerized state would respond to such exposure with cell division. A tolerized T-cell essentially will not respond by killing a cell presenting an antigen, a T-cell in the untolerized state would respond to such exposure by killing the cell presenting an antigen.

In one embodiment, the dendritic cell and/or a precursor thereof is provided with a glucocorticoid hormone in vitro. A T-cell of the invention is preferably an antigen specific T-cell, a cytotoxic T-cell or a Th cell.

In another aspect, the invention provides an isolated dendritic cell capable of modifying the function of an antigen specific Th cell, which would otherwise enhance a given immune response, resulting in a T-cell that is capable of reducing this immune response. In one embodiment, the invention provides a method for modifying an antigen specific T-cell comprising providing an dendritic cell according to the invention with said antigen and cocultivating said T-cell and said dendritic cell. Preferably, said cocultivating is performed in vitro. The method may further comprise multiplying the functionally modified T-cell.

The invention also provides an isolated functionally modified T-cell obtainable by a method according to the invention.

In another aspect, the invention provides the use of a glucocorticoid hormone for obtaining a dendritic cell capable of functionally modifying a T-cell.

The invention also provides a pharmaceutical composition comprising a dendritic cell and/or a functionally modified T-cell. The invention further provides the use of a dendritic cell and/or a functionally modified T-cell for the preparation of a medicament.

The invention also provides a method for the treatment of an individual suffering from, or at risk of suffering from, a disease associated with at least part of the immune system of the individual, including providing the individual with a dendritic cell and/or a functionally modified T-cell. Preferably, the dendritic cell and/or the functionally modified T-cell or precursors thereof are derived from an HLA-matched donor. Preferably, the HLA-matched donor is the individual.

Method of treatments of the invention are preferably used for the treatment of an individual suffering from an autoimmune disease, an allergy, a graft versus host disease and/or a host versus graft disease.

EXAMPLES

Example 1

Impairment of CD40-CD40L-Mediated Phenotypic Changes by DEX

Figure 1:
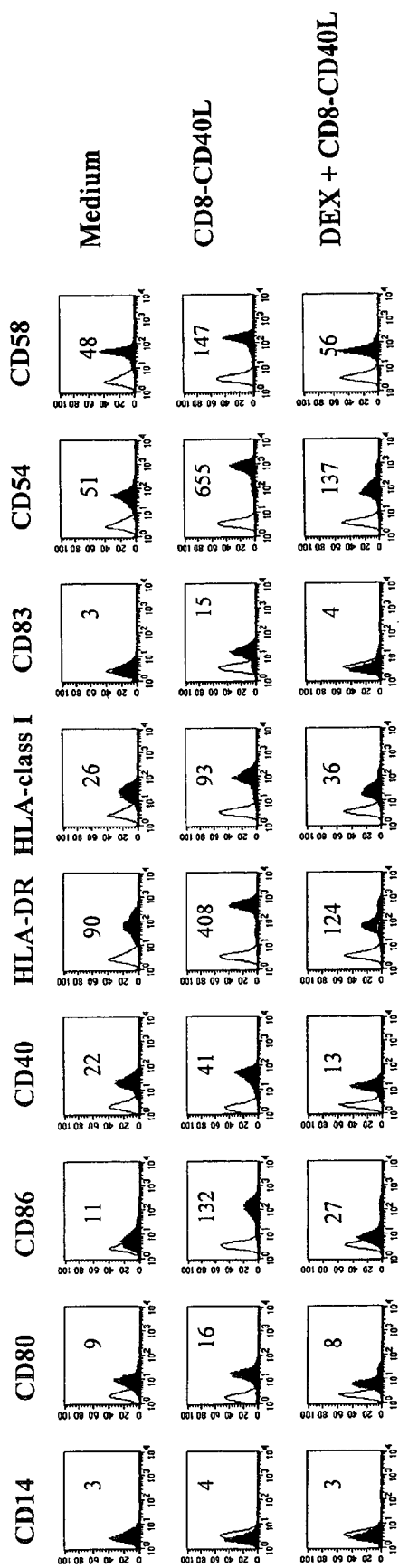
FIG. 1. Pretreatment with DEX inhibits the phenotypic changes induced by CD40 ligation.

We explored the impact of DEX on the phenotypic changes induced by CD40 ligation on immature monocyte-derived DC. In the absence of DEX the fusion protein CD8-CD40L induced a strong upregulation of the costimulatory molecules CD80, CD86 and CD40, of the MHC class I and II molecules, of the adhesion markers CD54 and CD58 and of the DC maturation marker CD83 (FIG. 1). In the presence of DEX, these CD8-CD40L-induced phenotypic changes were dramatically impaired: the upregulation of CD80, CD86, CD40, CD54, CD58 and of the MHC class I and II molecules was largely inhibited and CD83 was not expressed (FIG. 1). Importantly, DEX-treated DC did not revert to a monocyte/macrophage stage as shown by the lack of expression of CD14 (FIG. 1). Titration of DEX showed a complete inhibition of CD40-mediated phenotypic changes at $10^{-6}$ M and $10^{-7}$ M, a partial blockade at $10^{-8}$ M and no effect at $10^{-9}$ M and $10^{-10}$ (data not shown). In addition, DEX action was dependent on binding to the GC-receptor, since it was abolished by simultaneous addition of the GC receptor antagonist RU486 (data not shown). In experiments performed with LPS or TNF-a as activation agents, similar results were obtained. However, the combination of DEX and TNF-alpha induced a massive cell death (viable cell recovery 5-10% of control cultures), a phenomenon that was not observed when DEX-treated DC were stimulated with LPS or through CD40 (viable cell recovery 60 to 100% of control cultures) (not shown).

We next analyzed whether activated DC could still be affected by DEX. DC incubated with CD8-CD40L for 48 h and further exposed to DEX maintained a stable activated phenotype (FIG. 2).

We conclude that DEX prevents the phenotypic changes induced by CD40 signals on immature DC and that already activated DC are resistant to DEX action.

Example 2

DEX Does Not Interfere with the Regulation of DC Antigen Uptake Machinery

Unlike activated DC, immature DC efficiently internalize antigens through macropinocytosis and mannose receptor-mediated endocytosis (2, 3, 25, 26). We analyzed whether DEX could affect the DC antigen capture machinery and its downregulation following CD40 cross-linking. As shown in FIG. 3, incorporation of FITC-BSA and FITC-mannosylated BSA by immature DC and by DEX-treated immature DC was comparable. Upon CD40 triggering, a similar decrease of FITC-BSA and FITC-mannosylated BSA uptake by both DEX-treated and untreated DC was observed (FIG. 3). These results were the first to indicate to us that DEX does not block all aspects of DC activation, since it does not interfere with the down-regulation of the DC antigen capture machinery.

Example 3

DEX-Treated CD40-Triggered DC Secrete IL-10 Instead of IL-12

A key feature of CD40-triggered DC for initiating T-cell immunity resides in their ability to produce the proinflammatory cytokine IL-12 (5, 6, 27). We investigated whether DEX affected IL-12 production by DC stimulated through CD40, and we explored the possibility that DEX could promote the secretion of the anti-inflamatory cytokine IL-10. As shown in FIG. 4, CD40 triggering of DC strongly induced IL-12p40 and IL-12p70 secretion (up to 120 ng/ml and 170 pg/ml, respectively) but only poorly stimulated the production of IL-10 (up to 68 pg/ml). In contrast, CD40 triggering of DEX-treated DC resulted in a dramatically reduced IL-12p40 production (up to 100 fold) and in the complete suppression of IL-12p70 secretion, whereas IL-10 production was strongly enhanced (up to 50 fold) (FIG. 4). Immature DC and their DEX-treated counterparts failed to secrete detectable amounts of IL-12 and IL-10 (FIG. 4). Therefore, CD40 ligation of DC in the presence of DEX triggers the secretion of high levels of the anti-inflammatory cytokine IL-10 instead of IL-12.

Example 4

DEX-Treated CD40-Triggered DC are Capable of Suppressing Th1-Type Immunity

The strikingly modified response of DC to CD40 ligation in the presence of DEX prompted us to compare the T-cell stimulatory potential of these cells with that of their DEX-untreated counterparts. In an allogeneic MLR, CD40-triggered DC induced a strong proliferative T-cell response, whereas the addition of DEX prior to CD40 triggering reduced their T-cell stimulatory capacity to that of immature DC (FIG. 5). When tested for their ability to stimulate an hsp65-specific CD4$^+$ Th1 clone, CD40-triggered DC pulsed with the hsp65 protein or with the specific peptide epitope p3-13 were found to be potent inducers of both T-cell proliferation and T-cell dependent IFN-g production (FIG. 5). In contrast, in the presence of Ag-pulsed DEX-treated CD40-triggered DC, T-cell proliferation and IFN-g production were significantly decreased ($p<0.001$ and $p<0.01$ respectively) (FIG. 5). We next investigated whether DEX-treated CD40-triggered DC were simply poor stimulators of Th1 cells or whether they could exert suppressive effects on these T-cells. We, therefore, tested hsp65-specific T-cells stimulated with p3-13-pulsed DEX-treated CD40-triggered DC for their capacity to respond to a second potent antigenic challenge. FIG. 6 shows that preculturing T-cells with CD40-triggered DC led to a strong T-cell proliferation and IFN-gamma production upon second antigen-specific restimulation. In contrast, preculture with DEX-treated CD40-triggered DC resulted in a dramatically reduced proliferative and IFN-gamma production capacity of Th1 cells. Thus, CD40 triggering of DC in the presence of DEX results in APC that are not merely poor inducers of T-cell responses but that also induce a state of hyporesponsiveness in Th1 cells.

Materials and Methods

Generation of DC

Immature DC were generated from peripheral blood monocyte precursors (PBMC). Human PBMC from healthy donors, isolated through Ficoll-Hypaque density centrifugation were plated at $1.5 \times 10^7$ per well in 6-well plates (Costar Corp., Cambridge, Mass.) in RPMI 1640 (Life Technologies, Paisley, Scotland) supplemented with 2 mM glutamine, 100 UI/ml penicillin and 10% FCS. After 2 h at 37° C., the non-adherent cells were removed and the adherent cells were cultured in medium containing 500 U/ml IL-4 (Pepro Tech Inc. Rocky Hill, N.J.) and 800 U/ml GM-CSF (kindly provided by Dr S. Osanto, LUMC, Leiden, NL) for a total of 7 days.

Activation of Immature DC with a CD8-CD40L Fusion Protein

Activation of DC though CD40 was performed with a fusion protein made of the extracellular domain of human CD40L and of the murine CD8a chain (CD 8-CD40L). The CD8-CD40L cDNA described by Garrone et al. (23) was transferred into an eukaryotic expression vector containing the hygromycin resistance gene and used for the generation of stably transfected Chinese Hamster Ovary (CHO) cells. Culture supernatants containing the CD8-CD40L fusion protein were concentrated with a pressurized stirred cell system (Amicon, Inc., Beverly, Mass.), checked for binding to CD40 and tested for optimal DC activation conditions (not shown). DC were incubated at $5 \times 10^5$/ml/well in a 24-well plate (Costar Corp., Cambridge, Mass.) and activated in the presence of $\frac{1}{10}$ CD8-CD40L supernatant. Cells and supernatants were analyzed after 48 h. Of note, control supernatants obtained from untransfected CHO cells or from CHO cells transfected with the CD8a cDNA lacked DC activating functions and were similar to culture medium.

DEX and RU486 Treatment of DC

Seven days immature DC were treated with $10^{-6}$ M DEX (Sigma, St Louis, Mo.) in the presence of GM-CSF and IL-4 or GM-CSF alone. After 24 h, DC were analyzed or were further stimulated via CD40 by adding the CD8-CD40L fusion protein to the cultures as described above. In some experiments, the glucocorticoid receptor antagonist RU485 (Roussel-UCLAF, Romainville, France) was used at 10 mM final concentration, alone or in combination with DEX.

Analysis of DC Surface Phenotype by Flow Cytometry

Cells were stained on ice with FITC or PE-conjugated mouse monoclonal antibodies (MoAb) for 30 min in PBS 1% FCS and were analyzed on a FACScan® (Becton Dickinson, San Jose, Calif.). The following MoAb were used: FITC-anti-CD80 (BB1), PE-anti-CD86 (FUN-1), FITC-anti-CD40 (5C3), PE-anti-CD54 (HA 58) and PE-anti-CD58 (1C3) (Pharmingen, San Diego, Calif.); PE-anti-CD14 (L243) and PE-anti-HLA-DR (Mf-P9) (Becton Dickinson); PE-anti-CD83 (HB15A) (Immunotech, Marseille, France); and PE-anti-HLA class I (Tu 149) (Caltag Laboratories, Burlingame, Calif.).

Antigen Uptake Experiments

DC were resuspended in medium buffered with 25 mM Hepes. FITC-BSA and FITC-mannosylated BSA (both from Sigma) were added at 1 mg/ml final concentration and the cells were incubated at 37° C. or at 0° C. to determine background uptake. After 1 h, DC were washed extensively with ice-cold PBS and analyzed by FACS® using propidium iodide to eliminate dead cells.

Cytokine Detection by ELISA

Culture supernatants were analyzed in serial two-fold dilutions in duplicate. IL-12p70 was detected using a solid phase sandwich ELISA kit (Diaclone Research, Besancon, France) (sensitivity 3 pg/ml). For IL-12p40 and IFN-g detection, capture MoAb and polyclonal biotinylated detection Ab were obtained from Peter van de Meijde (BPRC, Rijswijk, NL)

(sensitivity 10 pg/ml). IL-10 was detected using the Pelikine compact human IL-10 ELISA kit (CLB, Amsterdam, NL) (sensitivity 3 pg/ml).

Allogeneic Mixed Lymphocyte Reaction (MLR)

Nonadherent allogeneic adult PBMC from an unrelated individual were cultured in 96-well flat-bottom plates (Costar Corp., Cambridge, Mass.) at a density of $1.5 \times 10^5$/well with various numbers of g-irradiated (3,000 rads) DC, in triplicate. Proliferation was assessed on day 5 by [3H]thymidine uptake (0.5 mCi/well, specific activity 5 Ci/mMol, Amersham Life Science, Buckinghamshire, UK) during a 16 h pulse.

Th1 Stimulation Assays

The Mycobacterium tuberculosis and *M. leprae* hsp65-specific, HLA-DR3-restricted CD4+ Th1 clone Rp15 1-1 used in this study recognizes an hsp65 determinant corresponding to peptide residues 3 to 13 (p3-13) (24). HLA-DR-matched DEX-treated immature DC and their DEX-untreated counterparts were pulsed with 10 mg/ml of p3-13 or with 10 mg/ml of hsp65 for 2 h, washed extensively and stimulated through CD40 as described above. For Ag-pulsed DEX-treated immature DC, CD40 triggering was performed in the presence of DEX. Hsp65 specific T-cells ($10^4$) were cultured with different numbers of g-irradiated (3,000 rads) DC in 96-well flat-bottom plates (Costar Corp.) in triplicate for 3 days. [$^3$H]thymidine (incorporation) was measured on day 3 after a 16 h pulse. Before the addition of [$^3$H]thymidine, 50 ml of supernatants were collected from each well and supernatants from triplicate wells were pooled to measure IFN-g production. To test hsp65-specific T-cells responsiveness to a second potent antigenic challenge, $10^4$ T-cells were first cultured for 48 h with $5 \times 10^3$ peptide-pulsed DC prepared as above then harvested and allowed to rest in medium containing 5 U/ml IL-2. Three days later, 10 viable T-cells were restimulated with $5 \times 10^3$ peptide-pulsed DC generated from the same donor as used for the first culture and tested for their ability to proliferate and to produce IFN-g as previously described.

Statistical Analysis

Covariance analysis was used to compare T-cell proliferation and IFN-g production as a function of DC number, between DEX-treated CD40-triggered DC and DEX-untreated CD40-triggered DC (FIG. 5).

REFERENCES

1. Bancherau J. Steinman R M: Dendritic cells and the control of immunity. Nature 392: 248, 1998.
2. Sallusto F, Lanzavecchia A: Efficient presentation of soluble antigen by cultured human dendritic cells is maintained by granulocyte/macrophage colony stimulating factor and downregulated by tumor necrosis factor a J Exp Med 179: 1109, 1994.
3. Sallusto F, Cella M, Danieli C, Lanzavecchia A: Dendritic cells use macropinocytosis and the mannose receptor to concentrate macromolecules in the major histocompatibility complex class II compartment: downregulation by cytokines and bacterial products. J Exp Med 182: 389, 1995.
4. Caux C, Massacrier C, Vandervliet B, Dubois B, van Kooten C, Durand I, Bancherau J: Activation of human dendritic cells through CD40 cross-linking. J Exp Med 180: 1263, 1994.
5. Cella M, Sheidegger D, Palmer-Lehman K, Lane P, Lanzavecchia A, Alber G: Ligation of CD40 on dendritic cells triggers production of high levels of interleukin-12 and enhances T-cell stimulatory capacity: T-T help via APC activation. J Exp Med 184: 747, 1996.
6. Koch F, Stanzl U, Jennevin P, Janke K, Heufler C, Kampgen E, Romani N, Schuler G: High levels IL-12 production by murine dendritic cells: upregulation via MHC class II and CD40 molecules and downregulation by IL-4 and IL-10. J Exp Med 184: 741, 1996.
7. Trinchieri G: Interleukin-12: a proinflammatory cytokine with immunoregulatory functions that bridge innate resistance and antigen-specific adaptive immunity. Annu Rev Immunol 13: 251, 1995.
8. Kamanaká M, Yu P, Yasui T, Koshida K, Kawaba T, Horii T, Kishimoto T, Kikutani H: Protective role of CD40 in Leishmania major infection at two distinct phases of cell-mediated immunity. Immunity 4: 275, 1996.
9. Yang Y, Wilson J M: CD40 ligand-dependent T-cell activation: requirement of B7-CD28 signaling through CD40. Science 273: 1862, 1996.
10. Mackey M F, Gunn J R, Ting P, Kikutani H, Dranoff G, Noelle R J, Barth Jr R J: Protective immunity induced by tumor vaccines requires interactions between CD40 and its ligand CD154 Cancer Res 57: 2569, 1997.
11. Grewal I S, Foellmer H G, Grewal K D, Xu J, Hardardottir F, Baron J L, Janeway Jr C A, Flavell R A: Requirement for CD40 ligand in costimulation induction, T-cell activation and experimental allergic encephalomyelitis. Science 273: 1864, 1996.
12. Kirk A D, Harlan D M, Armstrong N N, Davis T A, Dong Y, Gray G S, Hong X, Thomas D, Fechner J H, Knechtle S J: CTLA4-Ig and anti-CD40 ligand prevent renal allograft rejection in primates. Proc Natl Acad Sci USA 94: 8789, 1997.
13. Durie F H, Aruffo A, Ledbetter J, Crassi K M, Green W R, Fast L D, Noelle R J: Antibody to the ligand of CD40, gp39, blocks the occurrence of the acute and chronic forms of graft-vs-host disease. J Clin Invest 94: 1333, 1994.
14. Almawi W Y, Beyhum H N, Rahme A A, Rieder M J: Regulation of cytokine and cytokine receptor expression by glucocorticoids. J Leukoc Biol 60: 563, 1996.
15. Moser M, De Smedt T, Sornasse T, Tielemans F, and Chentoufi A A: Glucocorticoids down-regulate dendritic cell function in vitro and in vivo. Eur J Immunol 25: 2818, 1995.
16. Kitajima T, Ariitzumi K, Bergstresser P R, Takashima A A novel mechanism of glucocorticoid-induced immune suppression: the inhibition of T-cell-mediated terminal maturation of a murine dendritic cell line. J Clin Invest 98: 142, 1996.
17. Viera P L, Kalinski P, Wierenga E A, Kapsenberg M L, de Jong E C: Glucocorticoids inhibit bioactive IL-12p70 production by in vitro-generated human dendritic cells without affecting their T-cell stimulatory potential. J Immunol 161: 5245, 1998.
18. Romani N, Gruner S, Brang D, Kampgen E, Lenz A, Trockenbacher B, Konwalinka G, Fritsch P O, Steinman R M, Schuler G: Proliferating dendritic cell progenitors in human blood. J Exp Med 180: 83, 1994.
19. Randolph G C, Beaulieu S, Lebecque S, Steinman R M, Muller W A: Differentiation of monocytes into dendritic cells in a model of transendothelial trafficking. Science 282: 480, 1998.
20. Rissoan M C, Soumelis V, Kadowaki N, Grouard G, Briere F, de Waal Malefyt R, Liu Y-J: Reciprocal control of T helper cell and dendritic cell differentiation. Science 283: 1183, 1999.
21. Bender A, Sapp M, Schuler G, Steinman R M, Bhardwaj N: Improved methods for the generation of dendritic cells 21. from non proliferating progenitors in human blood. J Immunol Methods 196:121, 1996.
22. Romani N, Reider D, Heuer M, Ebner S, Kampgen E, Eibl B, Niederwieser D, Schuler G: Generation of mature dendritic cells from human blood: an improved method with special regard to clinical applicability. J Immunol Methods 196:137, 1996.
23. Garrone P, Neidhardt E-M, Garcia E, Galibert L, van Kooten C, Banchereau J: Fas ligation induces apoptosis of CD40-activated human B lymphocytes. J Exp Med 182: 1265, 1995.
24. Geluk A, van Meigaarden K E, Janson A A M, Drijfhout J-W, Meloen R, de Vries R R P, Ottenhoff T: Functional analysis of DR17(DR3)-restricted mycobacterial T-cell epitopes reveals DR17 binding motif and enables the design of allele-specific competitor peptides. J Immunol 149: 2864, 1992.
25. Engering A J, Cella M, Fluitsma D, Brockhaus M, Hoefsmit E C M, Lanzavecchia A, Pieters J: The mannose receptor functions as a high capacity and broad specificity antigen receptor in human dendritic cells. Eur J Immunol 27: 2412, 1997.
26. Tan M C A A, Mommaas A A, Drijfhout J-W, Jordens R, Onderwater J J M, Verwoerd D, Mulder A A, van der Heiden A N, Scheidegger D, Oomens L C J K Ottenhoff T H M, Tulp A, Neefjes J J, Koning F: Mannose receptor-mediated uptake of antigens strongly enhances HLA class II-restricted antigen presentation by cultured dendritic cells. Eur J Immunol 27: 2426, 1997.
27. de Saint Vis B, Fugier-Vivier I, Massacrier C, Gaillard C, Vanbervliet B, Ait-Yahia S, Banchereau J, Liu Y-J, Lebecque S, Caux C: The cytokine profile expressed by human dendritic, cells is dependent on cell subtype and mode of activation. J Immunol 160: 1666, 1998.
28. Piemonti L, Monti P, Allavena P, Sironi M, Soldini L, Leone B E, Socci C, Di Carlo V: Glucocorticoids affect human dendritic cell differentiation and maturation. J Immunol 162: 6473, 1999.
29. Blotta M H, Dekruyff R H, Umetsu D T: Corticosteroids inhibit IL-12 production in human monocytes and enhance their capacity to induce IL-4 synthesis in CD4+ lymphocytes. J Immunol 158: 5589, 1997.
30. Visser J, van Boxel-Dezaire A, Methrost D, Brunt T, de Kloet E R, Nagelkerken L: Differential regulation of interleukin 10 (IL-10) and IL-12 by glucocorticoids in vitro. Blood. 91: 4255, 1998.
31. van Kooten C, Banchereau J: Function of CD40 on B cells, dendritic cells and other cells. Curr Opin Immunol 9: 330, 1997.
32. Scheinman R I, Cogswell P C, Lofquist A K, and Baldwin Jr A S: Role of transcriptional activation of I kappa B alpha in mediation of immunosuppression by glucocorticoids. Science 270: 283, 1995.
33. Auphan N, Dinato J A, Rosette C, Helmberg A, Karin N: Immunosuppression by glucocorticoids: inhibition of NF-kappa B activity through induction of I kappa B synthesis. Science 270: 286, 1995.
34. Murphy T L, Cleveland M G, Kulesza P, Magram J, Murphy K M: Regulation of interleukin 12 p40 expression through an NF-kappa B half site. Mol Cell Biol 15: 5258, 1995.
35. Yoshimoto T, Nagase H, Ishida T, Inoue J, Nariuchi H: Induction of interleukin-12 p40 transcript by CD40 ligation via activation of nuclear factor-kappaB. Eur J Immunol 27: 3461, 1997.
36. Ridge J P, Di Rosa F, Matzinger P: A conditioned dendritic cell can be a temporal bridge between a CD4+ T-helper and a T-killer cell. Nature 393: 474, 1998.
37. Bennett S R, Carbone F R, Karamalis F, Flavell R A, Miller J F, Heath W R: Help for cytotoxic-T-cell responses is mediated by CD40 signalling. Nature 393: 478, 1998.
38. Schoenberger S P, Toes R E M, van der Voort E I, Offringa R, Melief C J M: T-cell help for cytotoxic T lymphocytes is mediated by CD40-CD40L interactions. Nature 393: 480, 1998.

The invention claimed is:

1. A method for preparing a pharmaceutical composition for reducing an unwanted T-cell response in a host, said method comprising:
culturing peripheral blood monocytes from said host to differentiate into dendritic cells;
activating said dendritic cells with a means for reducing IL-12p40 production by said dendritic cells;
loading said dendritic cells with an antigen against which said T-cell response is to be reduced; and
forming a pharmaceutical composition comprising said loaded, activated dendritic cells for administration to said host.

2. A method for preparing a pharmaceutical composition for reducing an unwanted T-cell response in a host against an antigen, said method comprising:
culturing peripheral blood monocytes from said host to differentiate into dendritic cells;
activating said dendritic cells with a glucocorticoid capable of activating a glucocorticoid receptor;
bringing said dendritic cells into contact with an antigen against which said T-cell response is to be reduced; and
forming a pharmaceutical composition comprising said loaded, activated dendritic cells.

3. The method according to claim 2, further comprising activating a CD40 receptor on said dendritic cells.

4. The method according to claim 3, wherein activating the CD40 receptor comprises incubating the dendritic cells with a substance selected from the group consisting of a CD8-40L fusion protein, a trimeric form of CD40L consisting of CD40L molecules to which a modified leucine zipper has been attached, anti-CD40 antibodies, and cells that express CD40L.

5. The method according to claim 2, wherein bringing said dendritic cells into contact with an antigen comprises incubating said dendritic cells with at least one peptide representing at least one antigen of interest before activating said dendritic cells with said substance capable of activating the glucocorticoid receptor.

6. The method according to claim 2, wherein bringing said dendritic cells into contact with an antigen comprises incubating said dendritic cells with cells containing at least one antigen of interest before activating said dendritic cells with said substance capable of activating the glucocorticoid receptor.

7. The method according to claim 2, wherein bringing said dendritic cells into contact with an antigen against which said T-cell response is to be reduced comprises loading said dendritic cells with at least one synthetic peptide representing at least one antigen of interest after activating said dendritic cells with said substance capable of activating the glucocorticoid receptor.

8. The method according to claim 2, wherein activating said dendritic cells with said substance capable of activating the glucocorticoid receptor comprises activating said dendritic cells such that said dendritic cells secrete interleukin-10.

9. The method according to claim 2, wherein said T-cell is a T-helper cell.

10. The method according to claim 2, wherein bringing said dendritic cells into contact with an antigen comprises incubating said dendritic cells with a cell homogenate containing at least one antigen of interest before activating said dendritic cells with said substance capable of activating the glucocorticoid receptor.

11. The method of claim 2, further comprising incubating the dendritic cells with a substance selected from the group consisting of lipopolysaccharide (LPS) and polyI/C.

12. The method of claim 2, wherein said glucocorticoid capable of activating the glucocorticoid receptor comprises dexamethasone.

13. A method for obtaining a dendritic cell capable of tolerizing a T-cell for an antigen, comprising:
   providing said dendritic cell with a substance capable of activating a glucocorticoid receptor;
   activating said dendritic cell; and
   providing said dendritic cell with said antigen, wherein said dendritic cell is capable of tolerizing a T-cell for said antigen.

14. The method according to claim 13, wherein providing said dendritic cell with the substance capable of activating a glucocorticoid receptor is in vitro.

15. The method according to claim 13, wherein providing said dendritic cell with said substance capable of activating the glucocorticoid receptor comprises providing a precursor of said dendritic cell with said substance capable of activating the glucocorticoid receptor in vitro.

16. The method according to claim 13, wherein said substance capable of activating the glucocorticoid receptor comprises dexamethasone.

17. The method according to claim 14, wherein said substance capable of activating the glucocorticoid receptor enhances secretion of IL-10 by said dendritic cells.

18. A method for preparing an isolated dendritic cell, said method comprising:
   isolating peripheral blood monocytes from a subject;
   culturing the peripheral blood monocytes to differentiate into dendritic cells;
   activating the dendritic cells with a glucocorticoid;
   loading the dendritic cells with an antigen; and
   isolating said loaded, activated dendritic cells.

19. The method according to claim 18, wherein the glucocorticoid is dexamethasone.

20. The method according to claim 18, wherein loading said dendritic cells with an antigen comprises loading said dendritic cells with an antigen defined by a response of a T-cell.

21. The method according to claim 18, wherein the antigen comprises an allogeneic antigen.

22. The method according to claim 21, wherein the glucocorticoid is dexamethasone.

23. The method according to claim 22, wherein loading said dendritic cells with an antigen comprises contacting said dendritic cells with cells derived from a graft or transplant donor.

24. The method according to claim 23, wherein the dendritic cells are derived from the graft or transplant recipient.

25. The method according to claim 18, further comprising incubating the dendritic cells with a substance selected from a group consisting of a CD8-40L fusion protein, a trimeric form of CD40L consisting of CD40L molecules to which a modified leucine zipper has been attached, anti-CD40 antibodies, and cells that express CD40L.

26. A method for preparing a dendritic cell capable of tolerizing a T-cell, said method comprising:
   culturing peripheral blood monocytes to differentiate into dendritic cells;
   activating the dendritic cells with dexamethasone; and
   loading the dendritic cells with an antigen which is MHC-matched to a clonal T-cell, wherein the dendritic cells are capable of tolerizing the clonal T-cell in vitro to the antigen.

27. A method for preparing a dendritic cell for tolerizing a T-cell in a graft or transplant recipient, said method comprising:
   culturing peripheral blood monocytes from said graft or transplant recipient to differentiate into dendritic cells;
   activating said dendritic cells; and
   loading said dendritic cells with an antigen against which said T-cell is to be tolerized.

28. The method according to claim 27, wherein activating said dendritic cells comprises administering a glucocorticoid.

29. The method according to claim 28, wherein activating said dendritic cells comprises administering dexamethasone.

30. The method according to claim 27, wherein loading said dendritic cells with an antigen comprises contacting said dendritic cells with cells derived from a graft or transplant donor.

31. A method for preparing a pharmaceutical composition for reducing an unwanted T-cell response to an antigen in a host, said method comprising:
   culturing peripheral blood monocytes from said host to differentiate into dendritic cells in vitro;
   contacting said dendritic cells in vitro with an antigen against which said T-cell response is to be reduced, thereby loading said dendritic cells with the antigen;
   contacting said dendritic cells with dexamethasone;
   activating the CD40 receptor on said dendritic cells; and
   forming a pharmaceutical composition comprising said loaded, activated dendritic cells.

32. The method according to claim 31, wherein activating the CD40 receptor comprises culturing the dendritic cells with a substance selected from the group consisting of a CD8-40L fusion protein, a trimeric form of CD40L comprising CD40L molecules having a modified leucine zipper covalently attached to said CD40L molecules, anti-CD40 antibody, and cells that express CD40L.

33. The method according to claim 31 further comprising contacting the dendritic cells with lipopolysaccharide (LPS) or polyI/C.

34. The method according to claim 31, comprising contacting said dendritic cells in vitro with an antigen against which said T-cell response is to be reduced before contacting said dendritic cells with dexamethasone.

35. The method according to claim 34, wherein contacting said dendritic cells in vitro with an antigen against which said T-cell response is to be reduced comprises co-culturing said dendritic cells and cells containing at least one antigen of interest.

36. The method according to claim 31, comprising contacting said dendritic cells in vitro with an antigen against which said T-cell response is to be reduced after contacting said dendritic cells with dexamethasone.

37. The method according to claim 36, wherein contacting said dendritic cells in vitro with an antigen against which said T-cell response is to be reduced comprises contacting said dendritic cells with at least one isolated peptide having at least one antigenic region of interest.

38. The method according to claim 34, wherein contacting said dendritic cells in vitro with an antigen against which said T-cell response is to be reduced comprises contacting said dendritic cells with a cell homogenate containing at least one antigen of interest.

39. A method for obtaining a dendritic cell capable of tolerizing a T-cell for an antigen, the method comprising:
contacting a dendritic cell with dexamethasone in vitro;
activating the dendritic cell through the CD40 receptor; and
contacting the dendritic cell with an antigen, thereby loading the dendritic cell with the antigen, and forming a dendritic cell capable of tolerizing a T-cell for the antigen.

40. The method according to claim 39, wherein the dendritic cell is derived from a graft or transplant donor.

41. The method according to claim 39, further comprising:
isolating peripheral blood monocytes from a subject;
culturing the peripheral blood monocytes to differentiate into dendritic cells;
incubating the dendritic cells with a substance selected from the group consisting of a CD8-40L fusion protein, a trimeric form of CD40L comprising CD40L molecules having a modified leucine zipper covalently attached to said CD40L molecules, anti-CD40 antibodies, cells that express CD40L, lipopolysaccharide (LPS) and polyI/C; and
isolating the dendritic cell.

42. The method according to claim 41, wherein contacting the dendritic cell with the antigen comprises contacting the dendritic cell with cells derived from a graft or transplant donor.

43. The method according to claim 41, wherein the peripheral blood monocytes are derived from the graft or transplant recipient.

* * * * *